United States Patent
Yamazaki et al.

(10) Patent No.: US 10,525,159 B2
(45) Date of Patent: Jan. 7, 2020

(54) LIQUID PREPARATION FOR CONTACT LENSES COMPRISING HYDROLYZED HYALURONIC ACID DERIVATIVE AND CATIONIC BACTERICIDE

(71) Applicant: OPHTECS CORPORATION, Kobe-shi, Hyogo (JP)

(72) Inventors: Katsuhide Yamazaki, Akashi (JP); Haruki Nakagawa, Kobe (JP)

(73) Assignee: OPHTECS CORPORATION, Kobe-shi (JP)

( * ) Notice: Subject to any disclaimer, the term of this patent is extended or adjusted under 35 U.S.C. 154(b) by 0 days.

(21) Appl. No.: 16/304,453

(22) PCT Filed: May 26, 2016

(86) PCT No.: PCT/JP2016/002558
§ 371 (c)(1),
(2) Date: Nov. 26, 2018

(87) PCT Pub. No.: WO2017/203550
PCT Pub. Date: Nov. 30, 2017

(65) Prior Publication Data
US 2019/0142990 A1    May 16, 2019

(51) Int. Cl.
*A61L 12/14* (2006.01)

(52) U.S. Cl.
CPC ........... *A61L 12/142* (2013.01); *A61L 12/143* (2013.01)

(58) Field of Classification Search
CPC .............................. A61L 12/142; A61L 12/143
See application file for complete search history.

(56) References Cited

U.S. PATENT DOCUMENTS

| | | | |
|---|---|---|---|
| 6,528,465 B1 * | 3/2003 | Cantoro | C11D 1/008 134/42 |
| 2008/0141628 A1 | 6/2008 | Lang et al. | |
| 2008/0306022 A1 | 12/2008 | Miyamoto et al. | |
| 2012/0316329 A1 * | 12/2012 | Fujikawa | A61K 8/345 536/53 |
| 2014/0102917 A1 | 4/2014 | Mori et al. | |

FOREIGN PATENT DOCUMENTS

| | | |
|---|---|---|
| JP | 2001-158734 A | 6/2001 |
| JP | 2003-2837 A | 1/2003 |
| JP | 2004-77953 A | 3/2004 |
| JP | 2008-209677 A | 9/2008 |
| JP | 2009-511423 A | 3/2009 |
| JP | 2011-213599 A | 10/2011 |
| JP | 2015-107993 A | 6/2015 |
| JP | 2015-166398 A | 9/2015 |
| JP | 5814181 B2 | 11/2015 |
| WO | 2008/076506 A1 | 6/2008 |
| WO | 2011/102462 A1 | 8/2011 |
| WO | 2013/031020 A1 | 3/2013 |

OTHER PUBLICATIONS

Petra Micochova, et al, Preparation and Characterization of Biodegradable Alkylether Derivatives of Hyaluronan, 69 Carbo. Polym. 344 (Year: 2007).*
Kudo et al., "Compatibility of Silicone Hydrogel Contact Lenses and Soft Contact Lens—Disinfecting Solutions", New Ophthalmology, 2005, vol. 22, No. 10, pp. 1349-1355, w/English translation (10 pages).
International Search Report dated Jul. 19, 2016, issued in counterpart International Application No. PCT/JP2016/002558 (2 pages).
Fujikawa, "Development of hyaluronan derivative having the effect of barrier function recovery" in Japanese, Fragrance Journal, Apr. 15, 2012, vol. 40, No. 4, pp. 41-43, (3 pages).
Extended Search Report dated Sep. 23, 2019, issued in counterpart EP Appliation No. 16903032.7. (6 pages).

* cited by examiner

*Primary Examiner* — Sean M Basquill
(74) *Attorney, Agent, or Firm* — Westerman, Hattori, Daniels & Adrian, LLP

(57) ABSTRACT

The present invention relates to a liquid preparation for soft contact lenses, particularly hydrogel contact lenses or silicone hydrogel contact lenses. The liquid preparation for contact lenses according to the present invention contains a hydrolyzed hyaluronic acid derivative having a monoether of a linear or branched alkyl group or alkenyl group having 6 or more and 20 or less carbon atoms and glycerol in a side chain. The liquid preparation for soft contact lenses according to the present invention may contain at least one cationic bactericide selected from the group consisting of an alexidine salt, a chlorhexidine salt, a polyhexamethylene biguanide salt and a quaternary ammonium salt. The liquid preparation for soft contact lenses according to the present invention is capable of suppressing adsorption of a cationic bactericide to soft contact lenses, and suppressing occurrence of corneal staining in a wearer.

6 Claims, 9 Drawing Sheets

[Fig. 1]
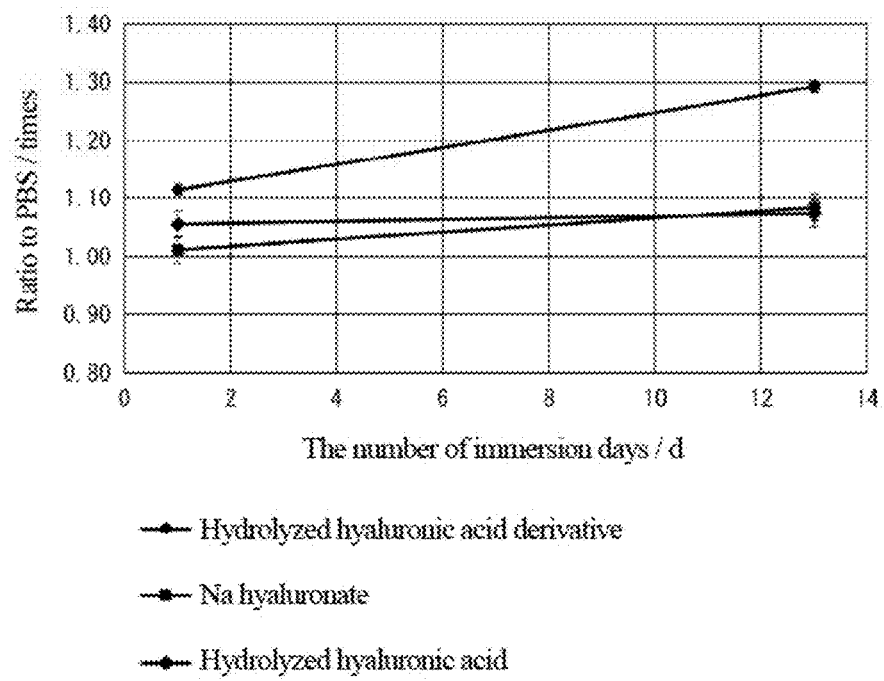
[Fig. 2]
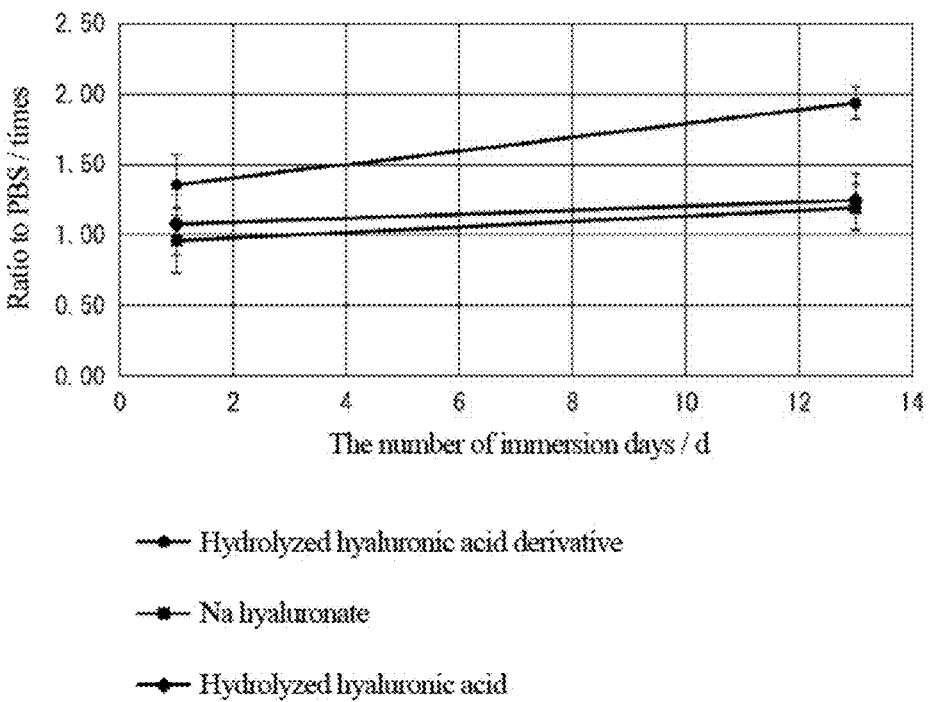

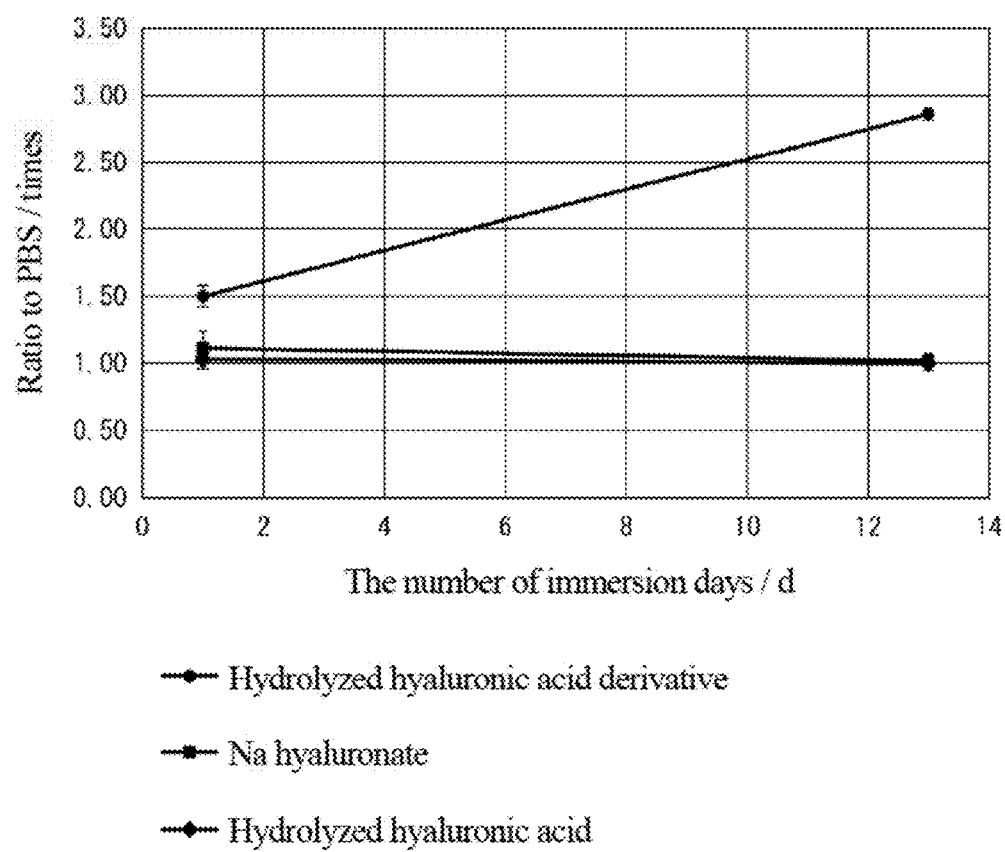
[Fig. 3]

[Fig. 4]
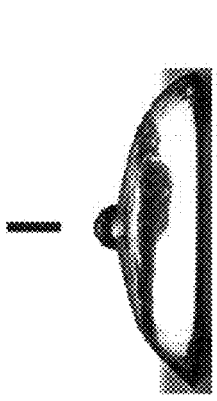

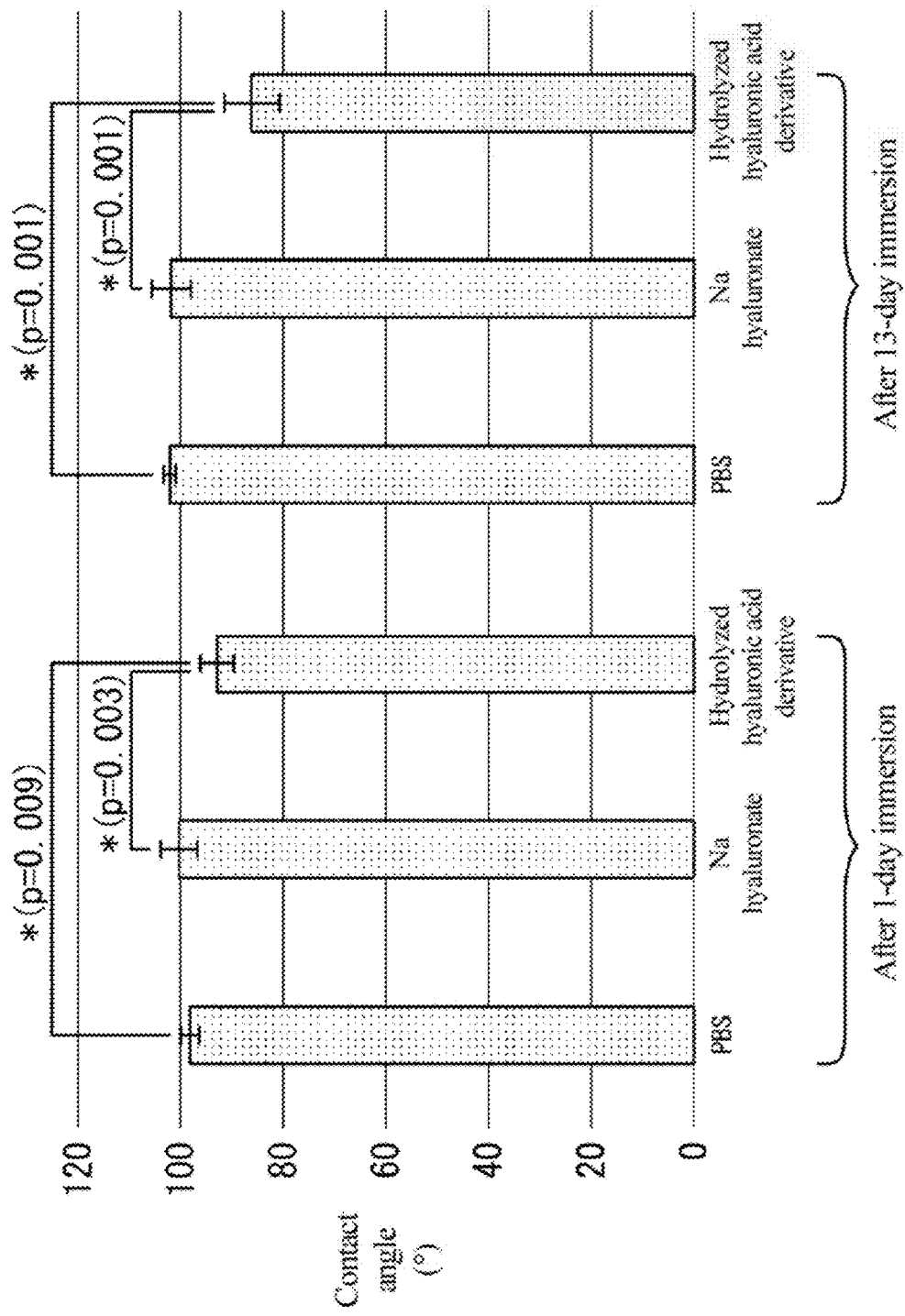
[Fig. 5]

[Fig. 6]
| PBS (1-day immersion) | Na hyaluronate (1-day immersion) | Hydrolyzed hyaluronic acid derivative (1-day immersion) |
|---|---|---|
| 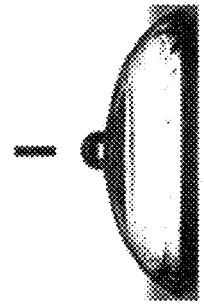 | 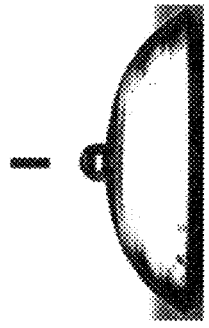 |  |
| PBS (13-day immersion) | Na hyaluronate (13-day immersion) | Hydrolyzed hyaluronic acid derivative (13-day immersion) |
| 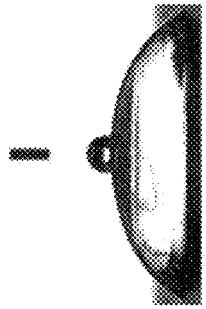 | 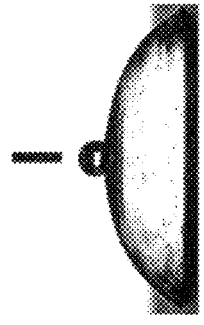 |  |

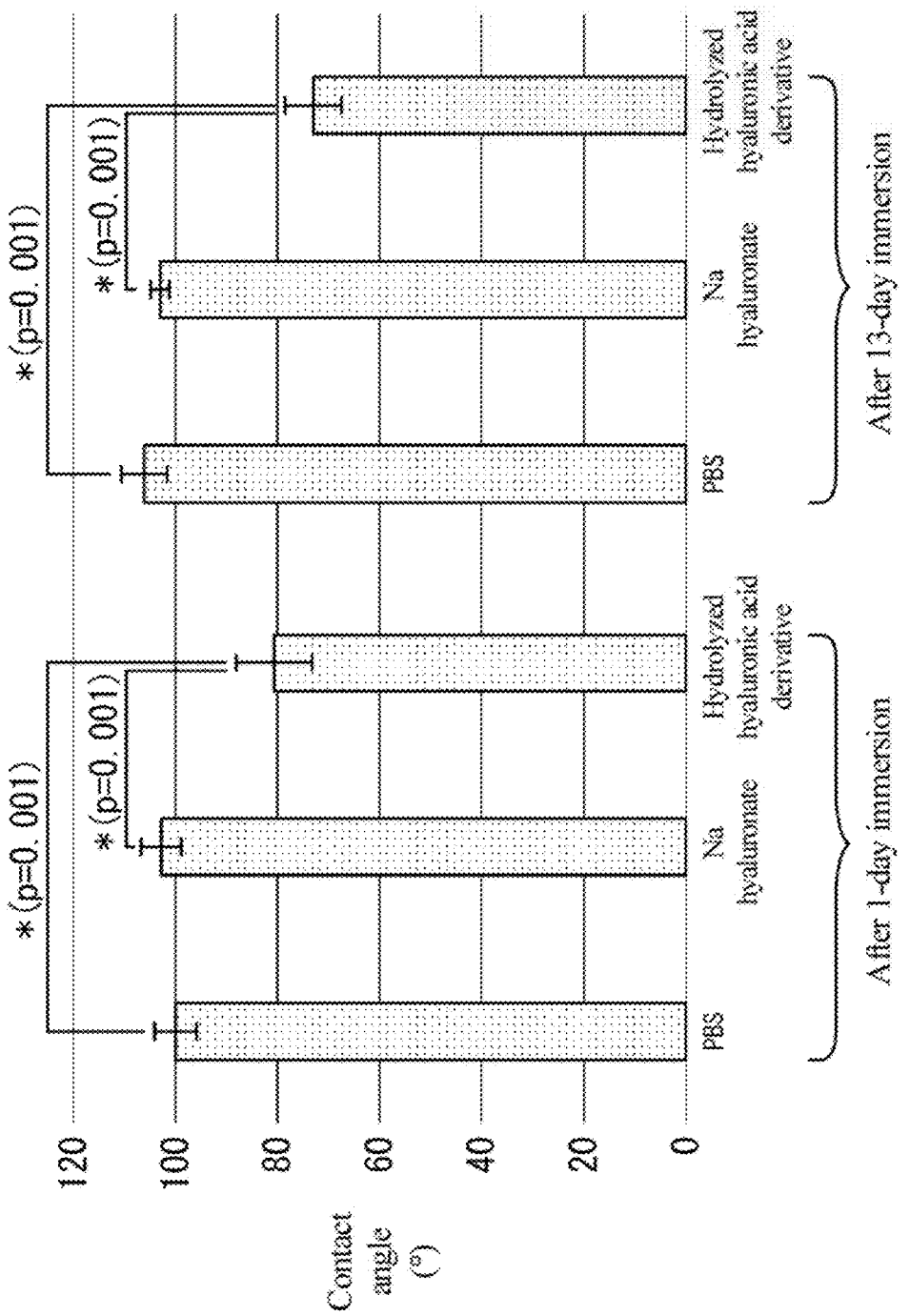
[Fig. 7]

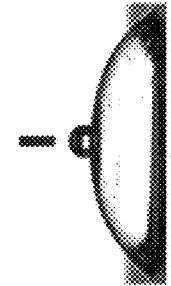
[Fig. 8]

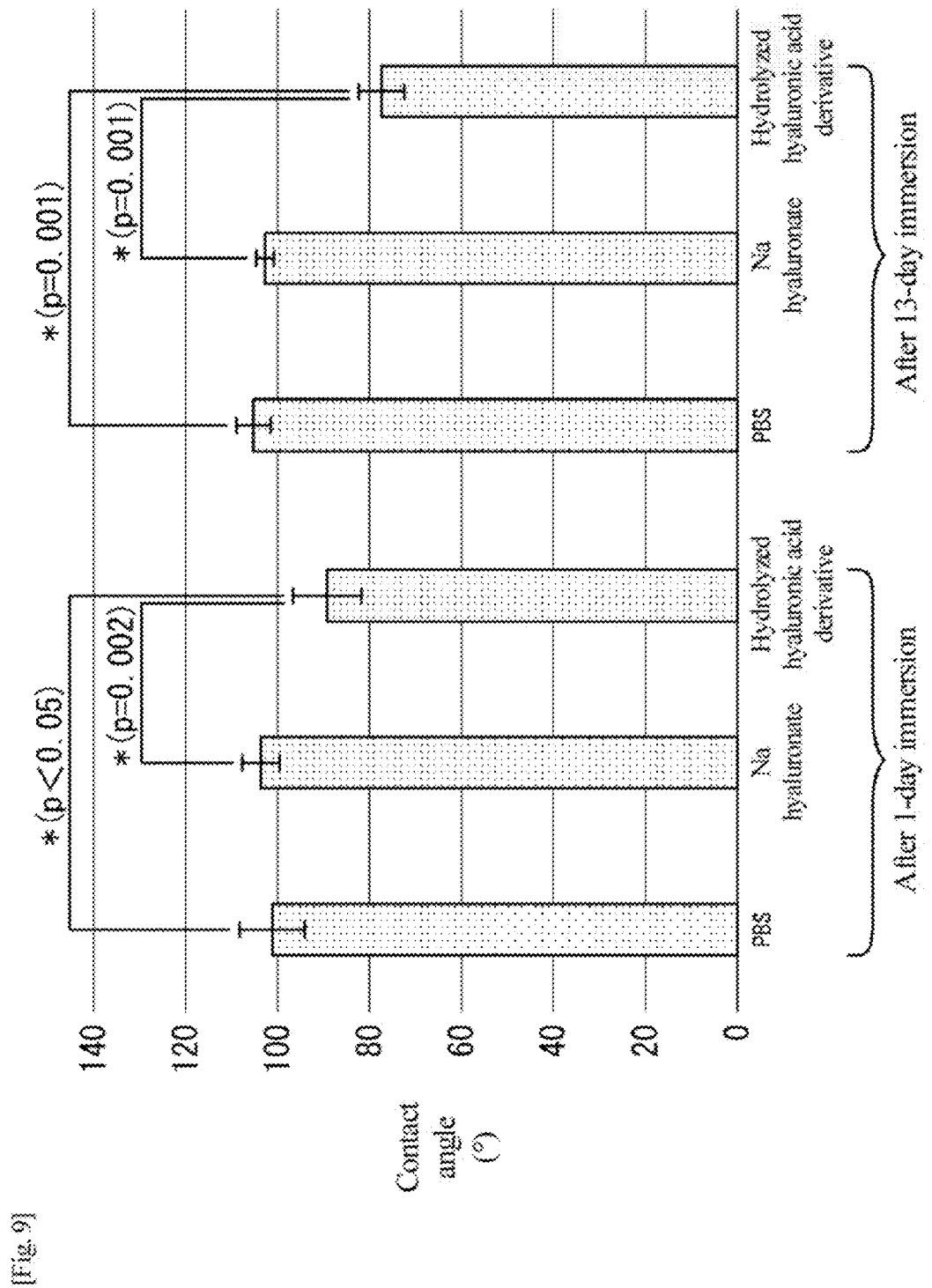
[Fig. 9]

[Fig. 10]
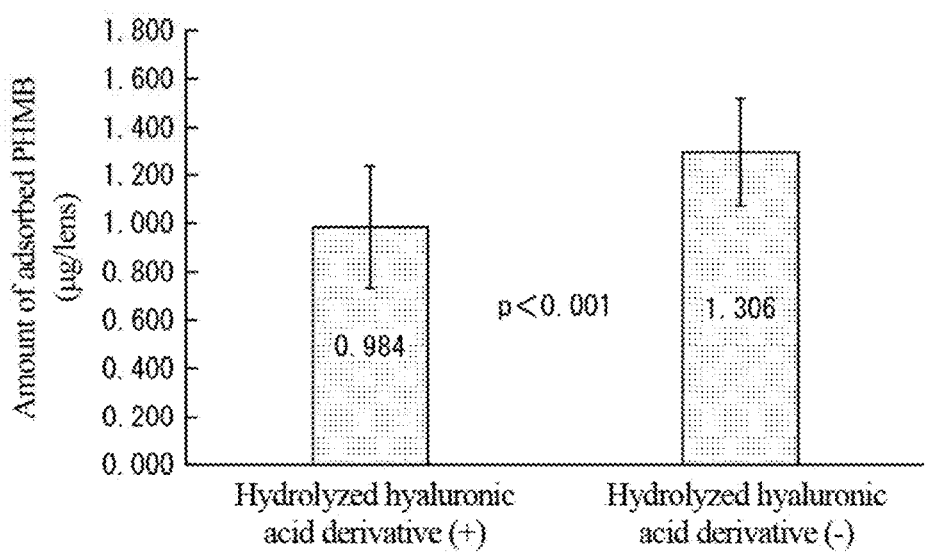
[Fig. 11]
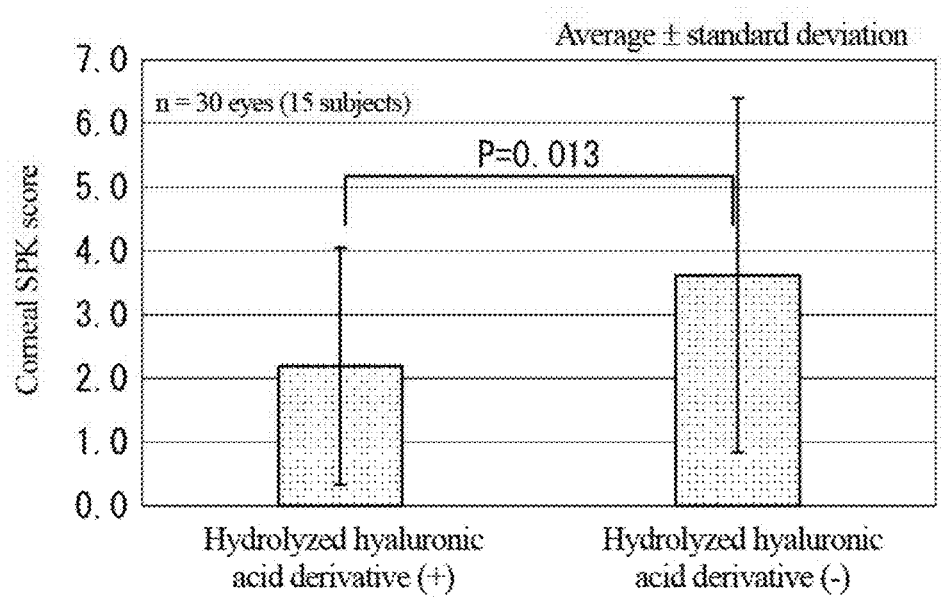

LIQUID PREPARATION FOR CONTACT LENSES COMPRISING HYDROLYZED HYALURONIC ACID DERIVATIVE AND CATIONIC BACTERICIDE

TECHNICAL FIELD

The present invention relates to a liquid preparation for contact lenses solution containing a cationic bactericide as a bactericide and a specific hydrolyzed hyaluronic acid derivative as a humectant (aqueous liquid preparation which can be used for all of cleaning agents, rinsing agents, bactericides, preservatives and wearing aids).

BACKGROUND ART

Wear of contact lenses may cause various troubles such as dry eye, eye strain, itching or hyperemia in the eye. Particularly, soft contact lenses are often worn over a long period of time because of favorable wearability. However, soft contact lenses generally have low oxygen permeability, and the user often complains about a feeling of dryness of eyes when wearing contact lenses. Patent Literature 1 discloses an ophthalmic composition for reducing a feeling of dryness in use of soft contact lenses, die ophthalmic composition containing vitamin A or vitamin D which is a fat-soluble vitamin Patent Literature 2 discloses an ophthalmic composition for soft contact lenses containing (A) vitamin A (B) panthenol. (C) a nonionic surfactant and polyhydric alcohol.

Silicone hydrogel contact lenses are contact lenses developed as soft contact lenses having high oxygen permeability. On the other hand, it has been reported that chlorobutanol which is used as a bactericide for contact lenses is very easily adsorbed to silicone hydrogel contact lenses. Patent Literature 3 discloses an ophthalmic composition for contact lenses which is capable of suppressing adsorption of chlorobutanol to silicone hydrogel contact lenses, die ophthalmic composition containing a combination of (A) chlorobutanol and (B) at least one selected from die group consisting of hyaluronic acid, chondroitin sulfide, alginic acid, hydroxypropylmethyl cellulose, and a salt thereof.

As an ophthalmic composition which can be safely used by a contact lens wearer, and has an excellent eye strain ameliorating effect and an excellent blurred vision ameliorating effect, Patent Literature 4 discloses an ophthalmic solution for wearing contact lenses which includes (A) at least one selected from the group consisting of a cellulose-based polymer compound, a vinyl-based polymer compound and dextran and (B) at least one selected font the group consisting of chondroitin sulfate, hyaluronic add, aspartic add, aminoethylsulfonic add, epsiton-aminocapioic add and a salt thereof. The ophthalmic solution for wearing contact lenses is used for both a solution for wearing contact lenses and an ophthalmic solution during wear of contact lenses with die same composition.

Non-Patent Literature 1 suggests that silicone hydrogel contact lenses may cause damage such as corneal staining when combined with some of multi-purpose solutions (MPS: disinfection solution capable of cleaning, rinsing preserving and disinfecting soft contact lenses in one solution), and the cause of such is considered to be based on compatibility of silicone hydrogel contact lenses with a bactericide.

CITATION LIST

Patent Literature

PTL 1: Japanese Patent Laid-Open Publication No. 2001-158734
PTL 2: Japanese Patent Laid-Open Publication No. 2011-213599
PTL 3: Japanese Patent Laid-Open Publication No. 2015-107993
PTL 4: Japanese Patent Laid-Open Publication No. 2015-166398

Non Patent Literature

NPL1: Kudo Masayiiti, Itoi Akira, New Ophthalmology, 22 (10): 1349-1355, 2005

SUMMARY OF INVENTION

Technical Problem

Although the compositions disclosed in Patent Literatures 1 and 4 have the effect of reducing a feeling of dryness in soft contact lens users, die effect is not sufficient. In addition, research itself has not sufficiently made progress on a phenomenon in which a bactericide contained in a composition (liquid preparation) for soft contact lenses is adsorbed to soft contact lenses, and adversely affect the eyes of a user, and studies have hardly beat conducted on means for suppressing adsorption of bactericide components to soft contact lenses.

Solution to Problem

The present inventors have extensively conducted studies on components added in MPS for reducing a feeling of dryness in a user during wear of soft contact lenses. Resultantly, die present inventors have found dial a hydrolyzed hyaluronic acid derivative having a specific structure (low-molecular-weight hyaluronic add derivative) has higher hydrophilicity imparting effect than that of hyaluronic add, and is capable of suppressing adsorption of a general-purpose bactericide to soft contact lenses, leading to completion of the present invention.

Specifically, the present invention relates to a liquid preparation for contact lenses containing a hydrolyzed hyaluronic add derivative, the hydrolyzed hyaluronic add derivative having a monoether of a linear or branched alkyl group or alkenyl group having 6 or more and 20 or less carbon atoms and glycerin in a side chain.

The liquid preparation for contact lenses according to the present invention is an aqueous liquid preparation which can be used as MPS for contact lenses or an artificial tear fluid, the liquid preparation containing as a humectant a hydrolyzed hyaluronic add derivative having a specific structure. The hydrolyzed hyaluronic add derivative having a specific structure (hydrolyzed alkyl glyceryl hyaluronate) for use in the presort invention exhibits a higher hydrophilicity imparting effect as compared with hyaluronic acid, and is capable of suppressing adsorption of a cationic bactericide to contact lenses.

Preferably; the liquid preparation for contact lenses according to the present invention preferably further contains at least one selected from the group consisting of an alexidine salt, a chlorhexidine salt, a polyhexamethylene biguanide salt and a quaternary ammonium salt as a cationic bactericide.

The liquid preparation for contact lenses according to the present invention is preferable particularly as a liquid preparation for soft contact lenses.

A content of the hydrolyzed hyaluronic add derivative in die liquid preparation fix contact lenses according to the present invention is preferably 5 ppm or more and 5000 ppm or less.

A concentration of foe cationic bactericide in foe liquid preparation for contact lenses according to the present invention is preferably 0.5 ppm or more and 50 ppm or less.

The hydrolyzed hyaluronic acid derivative is preferably a hydrolyzed hyaluronic add derivative having a chemical structure represented by the following chemical formula.

[Chemical Formula 1]

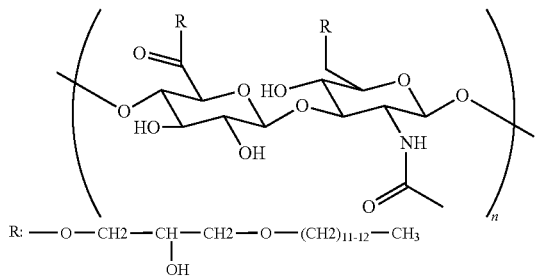

The liquid preparation for contact lenses according to foe present invention is preferably a liquid preparation for hydrogel contact lenses or silicone hydrogel contact lenses.

Advantageous Effects of Invention

According to the present invention, it is possible to prevent a feeling of dryness in a user during wear of contact lenses, and adsorption of a cationic bactericide to contact lenses, and suppress damage to the eyes of a user.

BRIEF DESCRIPTION OF DRAWINGS

FIG. 1 shows a graph obtained by plotting a relationship between foe number of days of immersion of SCL having etafilcon A as a material in a hydrolyzed hyaluronic acid derivative, Na hyaluronate and hydrolyzed hyaluronic add and a relative fluorescence intensity value.

FIG. 2 shows a graph obtained by plotting a relationship between foe number of days of immersion of SCL having balafilcon A as a material in a hydrolyzed hyaluronic acid derivative, Na hyaluronate and hydrolyzed hyaluronic add and a relative fluorescence intensity value.

FIG. 3 shows a graph obtained by plotting a relationship between die number of days of immersion of SCL having senofilcon A as a material in a hydrolyzed hyaluronic acid derivative, Na hyaluronate and hydrolyzed hyaluronic acid and a relative fluorescence intensity value.

FIG. 4 shows a photograph of a droplet on SCL having etafilcon A as a material, the photograph being taken by a dynamic contact angle measuring apparatus.

FIG. 5 shows a contact angle calculated from FIG. 4.

FIG. 6 shows a photograph of a droplet on SCL having balafilcon A as a material, the photograph being taken by a dynamic contact angle measuring apparatus.

FIG. 7 shows a contact angle calculated from FIG. 6.

FIG. 8 shows a photograph of a droplet on SCL having senofilcon A as a material, die photograph being taken by a dynamic contact angle measuring apparatus.

FIG. 9 shows a contact angle calculated from FIG. 8.

FIG. 10 shows a graph showing the amount of PHMB adsorbed per SCL when die SCL is immersed in solution A containing a hydrolyzed hyaluronic acid derivative represented by [Chemical formula 1] and solution B which does not contain the hydrolyzed hyaluronic add derivative.

FIG. 11 shows a graph showing SPK score measurement results for 15 subjects (30 eyes).

DESCRIPTION OF EMBODIMENTS

Embodiments of die present invention will be described with reference to die drawings as appropriate. The present invention is not limited to the following description.

The liquid preparation for contact lenses (CL) according to the present invention contains as essential constituent components (1) at least one cationic bactericide selected from the group consisting of an alexidine salt, a chlorhexidine salt, a polyhexamethylene biguanide salt and a quaternary ammonium salt; and (2) a hydrolyzed hyaluronic acid derivative having a monoether of a linear or branched alkyl group or alkenyl group having 6 or more and 20 or less carbon atoms and glycerin in the side chain. The liquid preparation fir CL according to die present invention may contain optional constituent components such as a pH adjuster or an osmotic pressure adjuster. As die optional components, known components that are used fir MPS for CL may be contained at normal concentrations.

The hydrolyzed hyaluronic acid derivative mentioned in die present invention is a compound obtained by hydrolyzing natural or synthetic hyaluronic add to reduce the molecular weight thereof and introducing a monether of a linear or branched alkyl or alkenyl group having 6 or more and 20 or less carbon atoms and glycerin to the side chain.

It suffices that the pH and osmotic pressure of die liquid preparation for CL according to die present invention fell within the range of the pH and osmotic pressure of normal MPS for CL.

As die cationic bactericide, polyhexamethylene biguanide, polyquarternium or alexidine is particularly preferable. The concentration of die bactericide in the liquid preparation for CL is preferably 0.5 ppm or mote and 50 ppm or less, more preferably 1 ppm or more and 20 ppm or less.

The carbon chain of the side chain of the hydrolyzed hyaluronic acid derivative is preferably a linear or branched alkyl group or alkenyl group having 6 or more and 20 or less carbon atoms, more preferably a linear alkyl group having 10 or more and 15 or less carbon atoms.

The concentration of die hydrolyzed hyaluronic add derivative in die liquid preparation fix CL is preferably 5 ppm or more and 5000 ppm or less, more preferably 20 ppm or more and 1000 ppm or less.

Most preferably; the hydrolyzed hyaluronic add derivative has a chemical structure represented by [Chemical Formula 1], The number of methylene groups in the side chain R is preferably 11 or 12.

Preferably, the hydrolyzed hyaluronic add derivative has an average molecular weight of 5000 or more and 10000 or less. Here, the average molecular weight means a value measured by the following method.

About 0.05 g of a sample is precisely weighed, and dissolved in a 02 mol/L sodium chloride solution, and die amount of die solution is adjusted to 100 mL accurately. The solution is taken in amounts of 8 mL 12 mL and 16 mL accurately, a 0.2 mol/L sodium chloride solution is added to each solution accurately to 20 mL, and the thus-obtained solutions are used as sample solutions. For the sample solution and die 0.2 mol/L sodium chloride solution, the specific viscosity is measured at 30.0±0.1° C. by the viscosity measurement method (first method: Capillary Viscometer Method) in General Test Method in die Japanese Pharmacopoeia (15th revision) (formula (A)), and the reduced viscosity at each concentration is calculated (formula (B)). The reduced viscosity is plotted on the ordinate, and the calculated concentration (g/100 mL) of the sample in the dried product is plotted on abscissa, and the intrinsic viscosity is determined from the intersection of the straight line connecting the points and the ordinate. The intrinsic viscosity determined here is substituted into die Laurent's equation (formula (Q) to calculate the average molecular weight (T C Laurent, M. Ryan, A Pietruszkiewicz, BRA, 42, 476-485(1960)).

<A Evaluation of Absorptivity Property of Hydrolyzed Hyaluronic Add Derivative to Soft Contact Lenses>

The absorptivity of the hydrolyzed hyaluronic add derivative represented by [Chemical Formula 1] to a soft contact lenses (SCL) was evaluated in the following procedure. As the hydrolyzed hyaluronic add derivative, HYORORIPEAR (registered trademark) manufactured by Kewpie Corporation which is a hydrolyzed hyaluronic add derivative represented by [Chemical Formula 1] was used. As hydrolyzed hyaluronic acid HYALO OLIGO (registered trademark, low molecular weight hyaluronic acid having an average molecular weight of 10,000 or less and obtained by hydrolyzing hyaluronic acid) manufactured by Kewpie Corporation was used. As sodium hyaluronate, HA-LQ manufactured by Kewpie Corporation was used.

Method for fluorescence-labeling hydrolyzed hyaluronic add derivative represented by [Chemical Formula 1]

[1. Preparation of Test Liquid to be Used]

(1) Preparation of 7.6 mM Aqueous Hydrolyzed Hyaluronic Add Derivative Solution 50 mL of purified water and 380 mg of the hydrolyzed hyaluronic add derivative (hydrolyzed alkyl (C12-13) glyceryl hyaluronate) represented by [Chemical formula 1] were put in a 200 mL beaker, and stirred and dissolved.

(2) Preparation of 9 mM Aqueous EDC Solution 225 mg of 1-ethyl-3-(3-dimethylaminopropyl) carbodiimide hydrochloride (EDC) was added in a 25 mL volumetric flask, and the volume was adjusted with purified water.

(3) 1. Preparation of 1.24 mM DMEQ-Hydrazide Solution 30 mL of N, N-dimethylformamide and 372 mg of 1,2,3,4-tetrahydro-6,7-dimethoxy-1-methyl-2-oxoquinoxaline-3-propionic acid hydrazide (DMEQ-hydrazide) was added in a 100 mL beaker, and stirred and dissolved.

[2. Fluorescence-labeling Reaction]

1.5 mL Dipyridine, 5 mL of a 9 mM aqueous EDC solution and 25 mL of a 1.24 mM DMEQ-hydrazide solution were added in tins order to a 7.6 mM aqueous hydrolyzed hyaluronic acid derivative solution with stirring. Thereafter, the mixture was stirred at room temperature under a light-shielding environment for 2 hours. After 2 hours, 50 mL of purified water was further added, and die mixture was stirred again for 10 minutes.

[3. Purification by Dialysis]

The liquid after fluorescence labeling reaction was added to a dialysis membrane, and the mixture was stirred in 5 L of purified water to perform dialysis, 12-hours dialysis was repeated four times. Purified water was exchanged every time.

[4. Drying and Sampling of Purified Liquid]

After completion of dialysis, die solution was transferred to an eggplant-shaped flask, and die solution was evaporated to dryness with an evaporator. The fluorescence-labeled hydrolyzed hyaluronic acid derivative deposited on die inner wall of die eggplant-shaped flask was scraped off and sampled. The sample is referred to as fluorescence-labeled sample 1.

Sodium hyaluronate and hydrolyzed hyaluronic add were fluorescence-labeled by performing die same operation as in die case of die hydrolyzed hyaluronic acid derivative represented by [Chemical Formula 1], These samples are referred to as fluorescence-labeled sample 2 and fluorescence-labeled sample 3, respectively.

(Method for Evaluating Absorptivity of Fluorescence-Labeled Hiaroripea Soft Contact Lens (SCL))

As SCL materials, etafilcon A (FDA Group IV) as a conventional hydrogel lens material, and senofilcon A (FDA Group I) and balafilcon A (FDA Group III) as silicone hydrogel lens materials were selected. The SCLs were immersed in solutions with fluorescence-labeled samples 1 to 3 dissolved in PBS at a final concentration of 50 ppm. As a control test, each SCL was immersed in PBS. The SCLs woe immersed in die respective solutions overnight, and then subjected to cycle treatment under the condition of immersion of die SCL in PBS for 8 hours in conformity to actual wear.

The cycle treatment was repeated, and die SCL at the first day and 13th day of immersion was used as a measurement sample. The fluorescence intensity was measured in accordance with "Method for evaluating absorptivity of fluorescence-labeled sample to SCL using fluorescence microscope" as described later, and absorptivity of each fluorescence-labeled sample to SCL was evaluated Three SCLs were used at each measurement point Each SCL was taken out from foe immersion liquid, then immersed in 2 mL of PBS for 5 minutes (repeated twice), and then used for the evaluation test.

(Method for Evaluating Absorptivity of Fluorescence-labeled Sample to SCL Using Fluorescence Microscope)

Amounting medium was dropped to two spots on a glass plate, and SCL cut into two halves was placed on the dropping spots, and covered with a cover glass. This was used as a specimen for a fluorescence microscope. The specimen was set on a fluorescence microscope (inverted research microscope IX71 manufactured by Olympus Corporation), four photographs were taken per SCL using a filter WU (excitation wavelength: 330 to 385 nm, fluorescence wavelength: 420 nm or more) with foe device set to a magnification ratio of 4 and camera shutter speed of 200 ms. Thereafter, the fluorescence intensity on the SCL was measured, and the measurement result was analyzed using image analysis software Image-J. Four contact lens portions on the photograph were randomly selected, the fluorescence intensity was measured in Image-J, and foe average and the standard deviation of the fluorescence intensity were then calculated. The measurement result is shown as a relative value where foe fluorescence intensity of the control test sample (SCL immersed in FBS) is 1. Statistic analysis was performed by the Mann-Whitney U test.

FIG. 1 shows a graph obtained by plotting a relationship between foe number of days of immersion of SCL having etafilcon A as a material in a hydrolyzed hyaluronic acid derivative, Na hyaluronate and hydrolyzed hyaluronic acid and a relative fluorescence intensity value. The fluorescence intensity of the hydrolyzed hyaluronic acid derivative 1 day after immersion was significantly different from the fluorescence intensity of Na hyaluronate and hydrolyzed hyaluronic acid at a risk ratio of less than 5%. The fluorescence intensity of the hydrolyzed hyaluronic acid derivative 13 days after immersion was significantly different from the fluorescence intensity of Na hyaluronate and hydrolyzed hyaluronic acid at a risk ratio of less than 5%. Further, the fluorescence intensity of foe hydrolyzed hyaluronic add derivative 13 days after immersion was significantly different from the fluorescence intensity of die hydrolyzed hyaluronic acid derivative 1 day after immersion at a risk ratio of less than 5%. On the other hand, the fluorescence intensities of Na hyaluronate and hydrolyzed hyaluronic add 13 days after immersion were not significantly different from those 1 day after immersion.

FIG. 2 shows a graph obtained by plotting a relationship between the number of days of immersion of SCL having balafilcon A as a material in a hydrolyzed hyaluronic add derivative, Na hyaluronate and hydrolyzed hyaluronic add and a relative fluorescence intensity value. The fluorescence intensity of the hydrolyzed hyaluronic acid derivative 1 day after immersion was significantly different from die fluorescence intensity of Na hyaluronate and hydrolyzed hyaluronic add at a risk ratio of less than 5%. The fluorescence intensity of the hydrolyzed hyaluronic acid derivative 13 days after immersion was significantly different from the fluorescence intensity of Na hyaluronate and hydrolyzed hyaluronic add at a risk ratio of less than 5%. Further, the fluorescence intensity of die hydrolyzed hyaluronic add derivative 13 days after immersion was significantly different from the fluorescence intensity of the hydrolyzed hyaluronic acid derivative 1 day after immersion at a risk ratio of less than 5%. On die other hand, die fluorescence intensities of Na hyaluronate and hydrolyzed hyaluronic add 13 days after immersion were not significantly different from those 1 day after immersion.

FIG. 3 shows a graph obtained by plotting a relationship between the number of days of immersion of SCL having senofilcon A as a material in a hydrolyzed hyaluronic add derivative, Na hyaluronate and hydrolyzed hyaluronic add and a relative fluorescence intensity value. The fluorescence intensity of die hydrolyzed hyaluronic acid derivative 1 day after immersion was significantly different from die fluorescence intensity of Na hyaluronate and hydrolyzed hyaluronic add at a risk ratio of less than 5% The fluorescence intensity of the hydrolyzed hyaluronic acid derivative 13 days after immersion was significantly different from die fluorescence intensity of Na hyaluronate and hydrolyzed hyaluronic add at a risk ratio of less than 5%. Further, the fluorescence intensity of die hydrolyzed hyaluronic add derivative 13 days after immersion was significantly different from the fluorescence intensity of die hydrolyzed hyaluronic add derivative 1 day after immersion at a risk ratio of less than 5%. On the other hand, the fluorescence intensities of Na hyaluronate and hydrolyzed hyaluronic add 13 days after immersion were not significantly different from those 1 day after immersion.

From FIGS. 1 to 3, it is confirmed that the hydrolyzed hyaluronic acid derivative represented by [Chemical Formula 1] is adsorbed in a lager amount to SOL having hydrogel or silicone hydrogel as a material as compared to Na hyaluronate or hydrolyzed hyaluronic acid. When the adsorption amount to SCL is large, the hydrophilicity of the SCL surface is increased to stabilize the tear fluid layer on SCL As a result, cationic disinfectant components hardly remain in SCL, and thus suppression of an adverse effect on the cornea can be expected.

<B. Evaluation of Hydrophilicity of Soft Contact Lens to which Hydrolyzed Hyaluronic Add Derivative is Adsorbed>

The hydrophilicity of SCL to which die hydrolyzed hyaluronic add derivative represented by [Chemical Formula 1] had been adsorbed was evaluated in die following procedure.

SCL having etafilcon A, senofilcon A or balafilcon A as a material was taken out from a blister pack. Moisture on SCL to be measured was wiped off twice with a paper waste cloth, and dien the contact angle was measured using a dynamic contact angle measuring apparatus (automatic contact angle meter DSA100 S manufactured by Krass Company). SCL was set on a sample stage of the dynamic contact angle measuring apparatus in such a manner that die concave surface of the SCL faced upward, and 2 µL of PBS was dropped After dropping, droplets were photographed with a camera after about 10 seconds, and the contact angle between the SCL surface and the droplet was calculated by analysis software.

Next, each SCL was immersed in a PBS solution containing 50 ppm of the hydrolyzed hyaluronic acid derivative. As a control test, each SCL was immersed in PBS. The SCLs were immersed in the respective solutions overnight, and then subjected to cycle treatment under the condition of immersion of the SCL in PBS for 8 hours in conformity to actual wear. The cycle treatment was repeated, and fir SCL 1 day after immersion and 13 days after immersion, the contact angle was calculated in die same manner as described above.

Further, each SCL was immersed in a PBS solution containing 50 ppm of Na hyaluronate instead of die hydrolyzed hyaluronic add derivative, and die contact angle was calculated in die same manner as in the case of the hydrolyzed hyaluronic acid derivative.

FIG. 4 shows a photograph of a droplet on SCL having etafilcon A as a material the photograph being taken by a dynamic contact angle measuring apparatus. FIG. 5 shows a contact angle calculated from FIG. 4. From FIG. 5, it is confirmed that SCL immersed in PBS containing 50 ppm of die hydrolyzed hyaluronic add derivative represented by [Chemical formula 1] has a significantly smaller contact angle, i.e. higher hydrophilicity, as compared to SCL immersed in PBS, or PBS containing 50 ppm of Na hyaluronate (Mann-Whitney U test). Further, it is also confirmed that SCL immersed for 13 days in PBS containing 50 ppm of the hydrolyzed hyaluronic add derivative represented by [Chemical formula 1] has a contact angle significantly smaller than that of SCL immersed in the PBS for 1 day at a risk ratio of less than 5% (Maim-Whitney U test).

FIG. 6 shows a photograph of a droplet on SCL having balafilcon A as a material, die photograph being taken by a dynamic contact angle measuring apparatus. FIG. 7 shows a contact angle calculated from FIG. 6. From FIG. 6, it is confirmed that SCL immersed in PBS containing 50 ppm of die hydrolyzed hyaluronic add derivative represented by [Chemical formula 1] has a significantly smaller contact angle, i.e. higher hydrophilicity, as compared to SCL immersed in PBS, or PBS containing 50 ppm of Na hyaluronate (Maim-Whitney U test). Further, it is also confirmed dial SCL immersed for 13 days in PBS containing 50 ppm of the hydrolyzed hyaluronic add derivative represented by [Chemical formula 1] has a contact angle significantly smaller than that of SCL immersed in die PBS for 1 day at a risk ratio of less than 5% (Mann-Whitney U test).

FIG. 8 shows a photograph of a droplet on SCL having senofilcon A as a material, die photograph being taken by a dynamic contact angle measuring apparatus. FIG. 9 shows a contact angle calculated from FIG. 8. From FIG. 6, it is confirmed that SCL immersed in PBS containing 50 ppm of die hydrolyzed hyaluronic acid derivative represented by [Chemical formula 1] has a significantly smaller contact angle, i.e. higher hydrophilicity, as compared to SCL immersed in PBS, or PBS containing 50 ppm of Na hyaluronate (Mann-Whitney U test). Further it is also confirmed that SCL immersed fix 13 days in PBS containing 50 ppm of the hydrolyzed hyaluronic acid derivative represented by [Chemical formula 1] has a contact angle significantly smaller than that of SCL immersed in the PBS for 1 day at a risk ratio of less than 5% (Maim-Whitney U test).

Thus, it is confirmed that for all of the three kinds of SCL, the hydrolyzed hyaluronic add derivative represented by [Chemical Formula 1] has a smaller contact angle, and a higher effect of increasing the hydrophilicity of the SCL surface as compared to Na hyaluronate. The absorptivity of the hydrolyzed hyaluronic acid derivative represented by [Chemical Formula 1] to SCL is supposed to be derived from hydrophobic groups of the derivative. As the frequency and degree of discomfort during wear of SCL is increased as the number of days on which SCL is worn increases, and therefore the hydrolyzed hyaluronic add derivative represented by [Chemical Formula 1] is more effective for reducing discomfort during wear of SCL than Na hyaluronate.

<C. Suppression of Adsorption of PHMB to Soft Contact Lens by Hydrolyzed Hyaluronic Add Derivative>

Polyhexamethylene biguanide (PHMB) is free of chlorine or an alcohol, odorless, non-bleaching and low-irritative, and die effect is hardly reduced even when organic contaminants are deposited. Thus, PHMB is commonly used for a SCL as a cationic bactericide having a high bactericidal effect against a wide range of bacteria. However, when PHMB is adsorbed to SCL, discomfort may be induced during wear of SCL Thus, the following test was conducted on whether the hydrolyzed hyaluronic add derivative represented by [Chemical formula 1] is capable of suppressing adsorption of PHMB to the SCL surface.

For a week, 15 subjects each wore SCL having Lotrafilcon B as a material on both eyes during the day, and at night, the SCL was immersed in solution A containing 50 ppm of the hydrolyzed hyaluronic acid derivative represented by [Chemical Formula 1] or in solution B which did not contain 50 ppm of the hydrolyzed hyaluronic acid derivative represented by [Chemical formula 1], Thereafter. SCL was recovered PHMB was extracted from SCL with FBS, PHMB was quantitatively determined by high performance liquid chromatography, and the amount of PHMB adsorbed to SCL was calculated Table 1 shows the compositions of solution A and solution B.

TABLE 1

| Component name | Solution A | Solution B |
| --- | --- | --- |
| Sodium chloride | 0.60% w/v | |
| Boric acid | 0.65% w/v | |
| Anhydrous sodium monohydrogenphosphate | 0.30% w/v | |
| Sodium edetate | 0.05% w/v | |
| Polyhexamethylene biguanide | 0.0001% w/v (1 ppm) | |
| Hydrolyzed hyaluronic acid derivative | 0.005% w/v (50 ppm) | 0 |
| Purified water | Appropriate amount | |
| Hydrochloric acid or sodium hydroxide | Appropriate amount | |

FIG. 10 shows a graph showing die amount of PHMB adsorbed per SCL when the SCL is immersed in solution A containing a hydrolyzed hyaluronic acid derivative represented by [Chemical formula 1] and solution B which does not contain the hydrolyzed hyaluronic add derivative. It is confirmed that the amount of PHMB adsorbed to SCL immersed in solution A containing the hydrolyzed hyaluronic add derivative represented by [Chemical Formula 1] is smaller than die amount of PHMB adsorbed to SCL immersed in solution B which does not contain die hydrolyzed hyaluronic add derivative represented by [Chemical formula 1], at a risk ratio of less than 1% (Mann-Whitney U test).

It is considered that since die hydrolyzed hyaluronic add derivative represented by [Chemical Formula 1] is structurally characterized by having a carboxyl group, die hydrolyzed hyaluronic add derivative repels cations when it adsorbed to die SCL surface, and therefore adsorption of a cationic bactericide to SCL is hindered. Thus, it is thought that adsorption of cationic bactericides other than PHMB to SCL can also be hindered.

<D. Suppression of Corneal Staining by Hydrolyzed Hyaluronic Add Derivative>

For a week, 15 subjects each wore SCL having Lotrafilcon B as a material on both eyes during die day, and at night, die SCL was immersed in solution A containing 50 ppm of the hydrolyzed hyaluronic add derivative represented by [Chemical Formula 1] or in solution B which did not contain 50 ppm of the hydrolyzed hyaluronic acid derivative represented by [Chemical Formula 1], Thereafter, both eyes of 15 subjects were examined by an ophthalmologist, and die SPK (superficial punctate keratitis) score was measured.

FIG. 11 shows a graph showing SPK scare measurement results for 15 subjects (30 eyes). Bis confirmed that die SPK score for solution A containing die hydrolyzed hyaluronic acid derivative represented by [Chemical Formula 1] is significantly lower than that for solution B which does not contain die hydrolyzed hyaluronic acid derivative represented by [Chemical formula 1] (Mann-Whitney U test). That is, die hydrolyzed hyaluronic acid derivative represented by [Chemical Formula 1] is confirmed to have an effect of suppressing occurrence of corneal staining.

INDUSTRIAL APPLICABILITY

The liquid preparation for CL according to the present invention is useful in the technical field of contact lenses as a solution for preserving or wearing hydrogel contact lenses or silicone hydrogel contact lenses.

The invention claimed is:

1. A liquid preparation for contact lenses comprising a hydrolyzed hyaluronic acid derivative, the hydrolyzed hyaluronic acid derivative having a chemical structure represented by the following chemical formula:

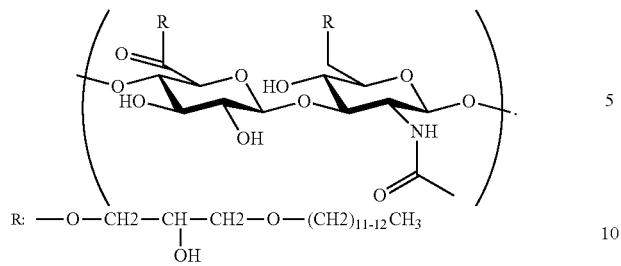

R: —O—CH2—CH(OH)—CH2—O—(CH2)$_{11-12}$CH$_3$

2. The liquid preparation for contact lenses according to claim 1, further comprising at least one selected from the group consisting of an alexidine salt, a chlorhexidine salt, a polyhexamethylene biguanide salt and a quaternary ammonium salt as a cationic bactericide.

3. The liquid preparation for contact lenses according to claim 1, which is a liquid preparation for soft contact lenses.

4. The liquid preparation for contact lenses according to claim 1, wherein a concentration of the hydrolyzed hyaluronic acid derivative is 5 ppm or more and 5000 ppm or less.

5. The liquid preparation for contact lenses according to claim 2, wherein a concentration of the cationic bactericide is 0.5 ppm or more and 50 ppm or less.

6. The liquid preparation for contact lenses according to claim 1, which is a liquid preparation for hydrogel contact lenses or silicone hydrogel contact lenses.

* * * * *